United States Patent
Cauldwell et al.

(10) Patent No.: US 8,597,328 B2
(45) Date of Patent: Dec. 3, 2013

(54) CANNULATED SUTURE ANCHOR

(75) Inventors: Nathan Cauldwell, Attleboro, MA (US); Jonathan Howe, Mansfield, MA (US); Eugene Wolf, San Francisco, CA (US)

(73) Assignee: DePuy Mitek, LLC, Raynham, MA (US)

( * ) Notice: Subject to any disclaimer, the term of this patent is extended or adjusted under 35 U.S.C. 154(b) by 0 days.

(21) Appl. No.: 12/749,109

(22) Filed: Mar. 29, 2010

(65) Prior Publication Data

US 2010/0185238 A1   Jul. 22, 2010

Related U.S. Application Data

(62) Division of application No. 11/555,545, filed on Nov. 1, 2006, now Pat. No. 8,114,128.

(51) Int. Cl.
*A61B 17/04* (2006.01)

(52) U.S. Cl.
USPC .......................................................... 606/232

(58) Field of Classification Search
USPC ............ 606/232, 300, 213; 623/23.72, 13.14; 411/387.5, 402
See application file for complete search history.

(56) References Cited

U.S. PATENT DOCUMENTS

| | | |
|---|---|---|
| 2,382,019 A | 8/1945 | Miller |
| 2,453,247 A | 11/1948 | Moss |
| 3,438,299 A | 4/1969 | Gutshall |
| 3,541,918 A | 11/1970 | Johnson |
| 3,762,418 A | 10/1973 | Wasson |
| RE28,111 E | 8/1974 | Laverty |
| 3,861,269 A | 1/1975 | Laverty |
| 4,175,555 A | 11/1979 | Herbert et al. |
| 4,241,638 A | 12/1980 | Shimizu et al. |
| 4,372,293 A | 2/1983 | Vijil-Rosales |
| 4,463,753 A | 8/1984 | Gustilo |
| 4,576,534 A | 3/1986 | Barth et al. |
| 4,632,100 A | 12/1986 | Somers et al. |
| 4,643,178 A | 2/1987 | Nastari et al. |
| 4,870,957 A | 10/1989 | Goble et al. |
| 4,946,468 A | 8/1990 | Li |
| 5,041,129 A | 8/1991 | Hayhurst et al. |

(Continued)

FOREIGN PATENT DOCUMENTS

| | | |
|---|---|---|
| EP | 046447 A1 | 2/1982 |
| EP | 067362 A1 | 12/1982 |

(Continued)

OTHER PUBLICATIONS

European Search Report, App. No. 08164065.8, mailed Aug. 18, 2010, 12 pages.

(Continued)

*Primary Examiner* — Corrine M McDermott
*Assistant Examiner* — Son Dang

(57) ABSTRACT

Methods and devices are provided for anchoring suture to bone. In one exemplary embodiment, a cannulated suture anchor is provided and it includes a suture-engaging member formed therein and configured to receive a suture therearound such that trailing ends of the suture can extend through the suture anchor. The present invention also provides exemplary sutures and drivers that can be used with the various methods and devices disclosed herein, or with other methods and devices known in the art.

18 Claims, 15 Drawing Sheets

(56) References Cited

U.S. PATENT DOCUMENTS

| | | |
|---|---|---|
| 5,100,417 A | 3/1992 | Cerier et al. |
| 5,152,790 A | 10/1992 | Rosenberg et al. |
| 5,156,616 A | 10/1992 | Meadows et al. |
| 5,176,682 A | 1/1993 | Chow |
| 5,258,016 A | 11/1993 | DiPoto et al. |
| 5,320,629 A | 6/1994 | Noda et al. |
| 5,336,231 A | 8/1994 | Adair |
| 5,370,662 A | 12/1994 | Stone et al. |
| 5,374,278 A | 12/1994 | Chesterfield et al. |
| 5,417,712 A | 5/1995 | Whittaker et al. |
| 5,423,860 A | 6/1995 | Lizardi et al. |
| 5,443,509 A | 8/1995 | Boucher et al. |
| 5,454,823 A | 10/1995 | Richardson et al. |
| 5,464,427 A | 11/1995 | Curtis et al. |
| 5,470,334 A | 11/1995 | Ross et al. |
| 5,486,197 A | 1/1996 | Le et al. |
| 5,505,736 A | 4/1996 | Reimels et al. |
| 5,527,322 A | 6/1996 | Klein et al. |
| 5,534,011 A | 7/1996 | Greene, Jr. et al. |
| 5,571,139 A | 11/1996 | Jenkins, Jr. |
| 5,573,547 A | 11/1996 | LeVeen et al. |
| 5,573,548 A | 11/1996 | Nazre et al. |
| 5,575,801 A | 11/1996 | Habermeyer et al. |
| 5,584,835 A | 12/1996 | Greenfield |
| 5,593,410 A | 1/1997 | Vrespa et al. |
| 5,601,557 A | 2/1997 | Hayhurst |
| 5,607,428 A | 3/1997 | Lin |
| 5,643,295 A | 7/1997 | Yoon |
| 5,674,230 A | 10/1997 | Tovey et al. |
| 5,707,395 A | 1/1998 | Li |
| 5,720,766 A | 2/1998 | Zang et al. |
| 5,733,307 A | 3/1998 | Dinsdale |
| 5,779,417 A | 7/1998 | Barth et al. |
| 5,782,864 A | 7/1998 | Lizardi |
| 5,814,070 A | 9/1998 | Borzone et al. |
| 5,851,219 A | 12/1998 | Goble et al. |
| 5,868,789 A | 2/1999 | Huebner |
| 5,891,168 A | 4/1999 | Thal |
| 5,895,351 A | 4/1999 | Nottage et al. |
| 5,916,224 A | 6/1999 | Esplin |
| 5,935,129 A | 8/1999 | McDevitt et al. |
| 5,941,882 A | 8/1999 | Jammet et al. |
| 5,957,953 A | 9/1999 | DiPoto et al. |
| 5,961,524 A | 10/1999 | Crombie |
| 6,001,101 A | 12/1999 | Augagneur et al. |
| 6,027,523 A | 2/2000 | Schmieding |
| 6,045,573 A | 4/2000 | Wenstrom, Jr. et al. |
| 6,096,060 A | 8/2000 | Fitts et al. |
| 6,117,162 A | 9/2000 | Schmieding et al. |
| 6,123,711 A | 9/2000 | Winters |
| 6,129,730 A | 10/2000 | Bono et al. |
| 6,139,565 A | 10/2000 | Stone et al. |
| 6,146,406 A | 11/2000 | Shluzas et al. |
| 6,149,653 A | 11/2000 | Deslauriers |
| 6,159,235 A | 12/2000 | Kim |
| 6,214,031 B1 | 4/2001 | Schmieding et al. |
| 6,234,797 B1 | 5/2001 | Ura |
| 6,261,292 B1 | 7/2001 | Diebold et al. |
| 6,264,677 B1 | 7/2001 | Simon et al. |
| 6,319,270 B1 | 11/2001 | Grafton et al. |
| 6,432,115 B1 | 8/2002 | Mollenauer et al. |
| 6,436,100 B1 | 8/2002 | Berger |
| 6,436,124 B1 | 8/2002 | Anderson et al. |
| 6,461,373 B2 | 10/2002 | Wyman et al. |
| 6,464,706 B1 | 10/2002 | Winters |
| 6,503,251 B1 | 1/2003 | Shadduck |
| 6,508,830 B2 | 1/2003 | Steiner |
| 6,554,852 B1 | 4/2003 | Oberlander |
| 6,569,186 B1 | 5/2003 | Winters et al. |
| 6,569,188 B2 | 5/2003 | Grafton et al. |
| 6,585,730 B1 | 7/2003 | Foerster |
| 6,610,080 B2 | 8/2003 | Morgan |
| 6,616,665 B2 | 9/2003 | Grafton et al. |
| 6,623,492 B1 | 9/2003 | Berube et al. |
| 6,652,563 B2 | 11/2003 | Dreyfuss |
| 6,656,183 B2 | 12/2003 | Colleran et al. |
| 6,660,023 B2 | 12/2003 | McDevitt et al. |
| 6,685,728 B2 | 2/2004 | Sinnott et al. |
| 6,699,250 B1 | 3/2004 | Osterle et al. |
| 6,770,076 B2 | 8/2004 | Foerster |
| 6,773,440 B2 | 8/2004 | Gannoe et al. |
| 6,773,450 B2 | 8/2004 | Leung et al. |
| 6,840,953 B2 | 1/2005 | Martinek |
| 6,923,824 B2 | 8/2005 | Morgan et al. |
| 7,090,690 B2 | 8/2006 | Foerster et al. |
| 7,217,279 B2 | 5/2007 | Reese |
| 7,306,614 B2 | 12/2007 | Weller et al. |
| 7,322,978 B2 | 1/2008 | West, Jr. |
| 7,390,328 B2 | 6/2008 | Modesitt |
| 7,473,252 B2 | 1/2009 | Barry |
| 7,556,640 B2 | 7/2009 | Foerster |
| 7,695,494 B2 | 4/2010 | Foerster |
| 2001/0004694 A1 | 6/2001 | Carchidi et al. |
| 2001/0037113 A1 | 11/2001 | Justin |
| 2001/0053913 A1 | 12/2001 | Freedland |
| 2002/0016594 A1 | 2/2002 | Schlapfer et al. |
| 2002/0052629 A1 | 5/2002 | Morgan et al. |
| 2002/0147463 A1 | 10/2002 | Martinek |
| 2002/0173822 A1 | 11/2002 | Justin et al. |
| 2002/0183751 A1 | 12/2002 | Justin et al. |
| 2003/0004545 A1 | 1/2003 | Burkhart et al. |
| 2003/0065332 A1 | 4/2003 | TenHuisen et al. |
| 2003/0065361 A1 | 4/2003 | Dreyfuss |
| 2003/0074002 A1 | 4/2003 | West |
| 2003/0088252 A1 | 5/2003 | Kaikkonen et al. |
| 2003/0125745 A1 | 7/2003 | Tseng et al. |
| 2003/0144696 A1 | 7/2003 | Sinnott et al. |
| 2003/0158555 A1 | 8/2003 | Sanders et al. |
| 2003/0187446 A1 | 10/2003 | Overaker et al. |
| 2003/0187477 A1 | 10/2003 | Lintner |
| 2003/0229350 A1 | 12/2003 | Kay |
| 2004/0006346 A1 | 1/2004 | Holmen et al. |
| 2004/0098050 A1 | 5/2004 | Foerster et al. |
| 2004/0106949 A1 | 6/2004 | Cohn et al. |
| 2004/0116963 A1 | 6/2004 | Lattouf |
| 2005/0107828 A1 | 5/2005 | Reese |
| 2005/0119698 A1 | 6/2005 | Martinek |
| 2005/0222618 A1 | 10/2005 | Dreyfuss et al. |
| 2005/0222619 A1 | 10/2005 | Dreyfuss et al. |
| 2005/0267479 A1 | 12/2005 | Morgan et al. |
| 2005/0283158 A1 | 12/2005 | West |
| 2006/0079904 A1 | 4/2006 | Thal |
| 2006/0099109 A1 | 5/2006 | Olofsson et al. |
| 2006/0100630 A1 | 5/2006 | West |
| 2006/0276841 A1* | 12/2006 | Barbieri et al. ............... 606/232 |
| 2006/0282083 A1 | 12/2006 | Fanton et al. |
| 2007/0060922 A1 | 3/2007 | Dreyfuss |
| 2007/0073299 A1 | 3/2007 | Dreyfuss et al. |
| 2007/0203498 A1 | 8/2007 | Gerber et al. |
| 2007/0213730 A1 | 9/2007 | Martinek et al. |
| 2007/0219557 A1 | 9/2007 | Bourque et al. |
| 2007/0219558 A1 | 9/2007 | Deutsch |
| 2007/0225719 A1 | 9/2007 | Stone et al. |
| 2007/0233122 A1 | 10/2007 | Denis et al. |
| 2007/0282341 A1 | 12/2007 | Hes et al. |
| 2007/0288025 A1 | 12/2007 | Peukert et al. |
| 2008/0004659 A1 | 1/2008 | Burkhart et al. |
| 2008/0009904 A1 | 1/2008 | Bourque et al. |
| 2008/0147063 A1 | 6/2008 | Cauldwell et al. |
| 2008/0147064 A1 | 6/2008 | Cauldwell et al. |
| 2008/0147119 A1 | 6/2008 | Cauldwell et al. |
| 2009/0076544 A1 | 3/2009 | DiMatteo et al. |
| 2009/0076545 A1 | 3/2009 | DiMatteo et al. |

FOREIGN PATENT DOCUMENTS

| | | |
|---|---|---|
| EP | 0464479 A | 1/1992 |
| EP | 0465910 | 1/1992 |
| EP | 465910 A1 | 1/1992 |
| EP | 0673624 A | 9/1995 |
| EP | 0464479 A2 | 8/2004 |
| EP | 1448543 A1 | 8/2004 |
| EP | 1719450 A1 | 11/2006 |
| GB | 1448543 A | 9/1976 |

(56) References Cited

FOREIGN PATENT DOCUMENTS

| | | | |
|---|---|---|---|
| JP | 09-056727 | A | 3/1997 |
| JP | 2006-512144 | A | 4/2006 |
| WO | 97/30649 | A | 8/1997 |
| WO | 0209601 | A2 | 2/2002 |
| WO | 03029237 | A1 | 4/2003 |
| WO | WO-03070108 | A1 | 8/2003 |
| WO | 2004/060173 | A1 | 7/2004 |
| WO | 2006073624 | A1 | 7/2006 |
| WO | 2006099109 | A2 | 9/2006 |

OTHER PUBLICATIONS

European Search Report Application No. 07254115.4 dated Apr. 11, 2008.
Office Action mailed May 13, 2010—U.S. Appl. No. 11/555,545.
Office Action dated Aug. 25, 2010, U.S. Appl. No. 11/855,670.
Office Action dated Sep. 3, 2010, U.S. Appl. No. 11/555,557.
Office Action dated Nov. 1, 2010 for U.S. Appl. No. 11/555,568.
Office Action dated Aug. 17, 2010, U.S. Appl. No. 11/855,728.
Office Action dated Aug. 16, 2010, U.S. Appl. No. 11/555,545.
Office Action mailed Oct. 5, 2009, U.S. Appl. No. 11/555,545.
Office Action mailed Dec. 17, 2008, U.S. Appl. No. 11/555,545.
Office Action mailed May 19, 2009, U.S. Appl. No. 11/555,545.
Office Action mailed May 11, 2009, U.S. Appl. No. 11/555,557.
Office Action mailed Jul. 23, 2009, U.S. Appl. No. 11/555,557.
Office Action mailed Dec. 17, 2008, U.S. Appl. No. 11/555,557.
Office Action mailed Dec. 22, 2009, U.S. Appl. No. 11/555,557.
Office Action mailed Dec. 31, 2008, U.S. Appl. No. 11/555,568.
Office Action mailed Aug. 18, 2009, U.S. Appl. No. 11/555,568.
Partial European Search Report, Application No. 08164065.8, mailed Mar. 29, 2010, 7 pages.
European Search Report Application No. 07254114.7 dated Dec. 28, 2007.
Office Action mailed Mar. 23, 2010, U.S. Appl. No. 11/855,670.
Office Action mailed Mar. 4, 2010, U.S. Appl. No. 11/855,728.
Canadian Examiner's Requisition, CA Appln. No. 2,608,903, dated Mar. 8, 2010.
Japanese Office Action issued Jun. 26, 2012 for Application No. 2007-283568 (5 pages).
Japanese Office Action issued Jul. 31, 2012 for Application No. 2007-283534 (9 pages).

* cited by examiner

FIG. 11A
FIG. 11B
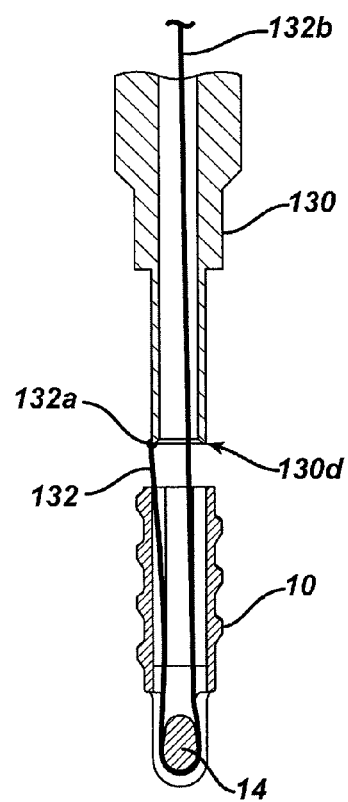
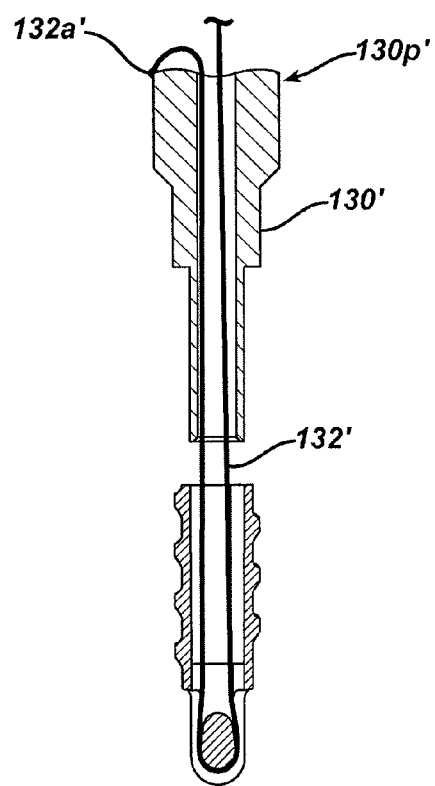

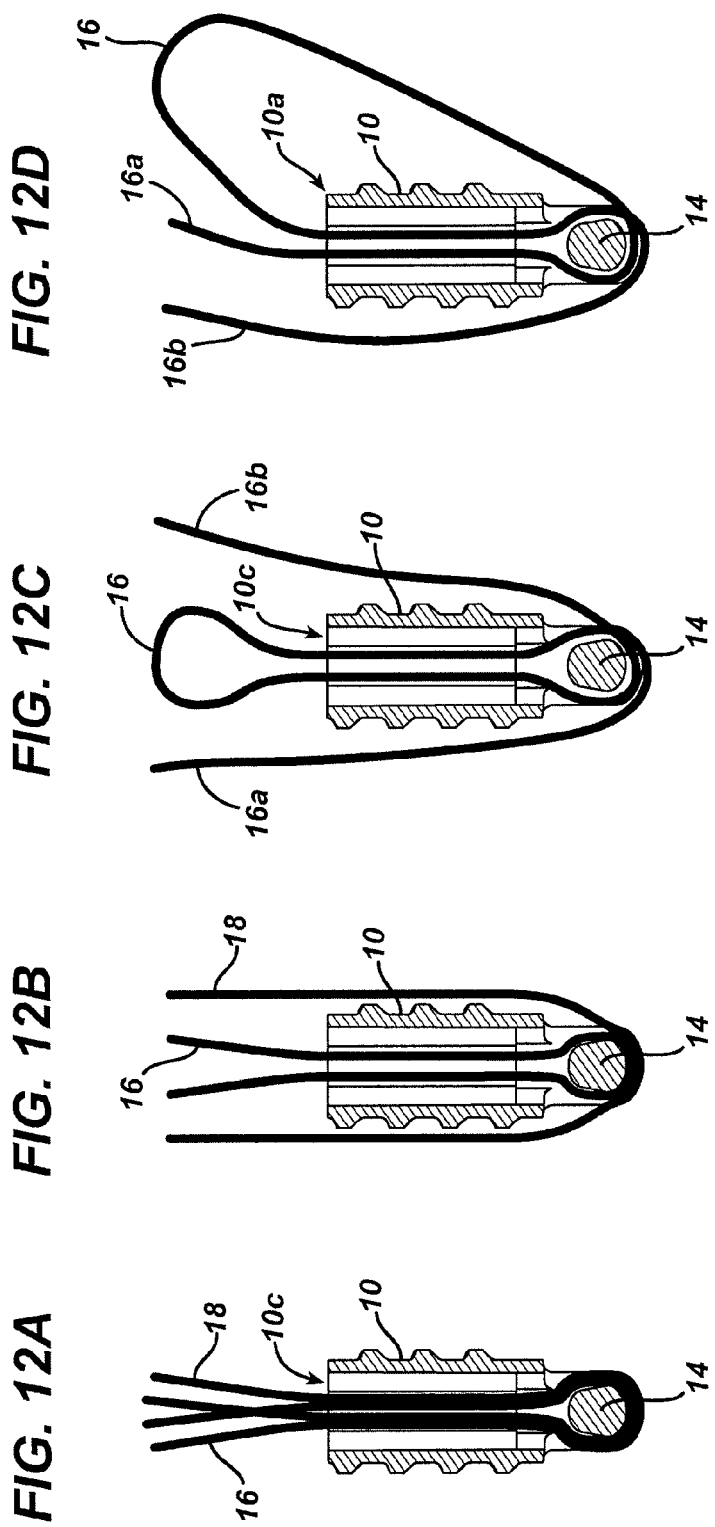

CANNULATED SUTURE ANCHOR

CROSS REFERENCE TO RELATED APPLICATIONS

The present application is a divisional of U.S. application Ser. No. 11/555,545 filed on Nov. 1, 2006 U.S. Pat. No. 8,114,128 and entitled "Cannulated Suture Anchor," which is hereby incorporated by reference in its entirety.

FIELD OF THE INVENTION

The present invention relates generally to medical devices and procedures, and more particularly to systems and methods for attaching soft tissue to bone.

BACKGROUND OF THE INVENTION

The complete or partial detachment of ligaments, tendons and/or other soft tissues from their associated bones within the body are relatively commonplace injuries, particularly among athletes. Such injuries are generally the result of excessive stresses being placed on these tissues. By way of example, tissue detachment may occur as the result of an accident such as a fall, over-exertion during a work-related activity, during the course of an athletic event, or in any one of many other situations and/or activities.

In the case of a partial detachment, the injury will frequently heal itself, if given sufficient time and if care is taken not to expose the injury to further undue stress. In the case of complete detachment, however, surgery may be needed to re-attach the soft tissue to its associated bone or bones. Numerous devices are currently available to re-attach soft tissue to bone. Examples of such currently-available devices include screws, staples, suture anchors and tacks. In soft tissue re-attachment procedures utilizing screws, the detached soft tissue is typically moved back into its original position over the bone. Then the screw is screwed through the soft tissue and into the bone, with the shank and head of the screw holding the soft tissue to the bone. Similarly, in soft tissue re-attachment procedures utilizing staples, the detached soft tissue is typically moved back into its original position over the bone. Then the staple is driven through the soft tissue and into the bone, with the legs and bridge of the staple holding the soft tissue to the bone.

In soft tissue re-attachment procedures utilizing suture anchors, an anchor-receiving hole is generally first drilled in the bone at the desired point of tissue re-attachment. Then a suture anchor is deployed in the hole using an appropriate installation tool. This effectively locks the suture to the bone, with the free end(s) of the suture extending out of the bone. The free ends of the suture are passed through or around the soft tissue and are used to tie the soft tissue securely to the bone.

While current suture anchors are effective in anchoring soft tissue to bone, one drawback with current devices is that the suture anchor must have a head with a length that is sufficient to withstand a torque applied thereto by a driver. As a result of the increased length, the suture anchor will typically extend at least partially into underlying soft cancellous bone in order to position the head beneath the outer surface of the bone. The bone-engaging portion of the suture anchor will thus be mostly disposed within and engaged with cancellous bone, rather than cortical bone. This is due to the fact that the cortical bone is only about 1 mm to 3 mm in length, and the driver head is often longer than 3 mm. Once implanted, tension applied to the anchor via the sutures can cause the anchor to migrate into the cortical bone and thus the head of the suture anchor can become proud, resulting in a weak fixation among other problems.

Accordingly, there remains a need for improved methods and devices for attaching soft tissue to bone.

SUMMARY OF THE INVENTION

In one embodiment, a suture anchor is provided having an elongate body with proximal and distal ends and an inner lumen extending therethrough. At least one bone-engaging surface feature, such as a thread, can be formed on at least a portion of an external surface thereof for engaging bone. The inner lumen of the elongate body can include a suture-engaging member extending substantially transverse to an axis of the inner lumen and adapted to receive a suture therearound such that a suture can extend around the suture-engaging member and trailing ends of the suture can extend through the inner lumen and out of the proximal end of the elongated body.

The elongate body can have a variety of configurations. In one embodiment, the elongate body can include cut-outs formed in opposed sidewalls thereof and extending proximally from the distal end of the elongate body. The cut-outs can be in communication with the inner lumen. In an exemplary embodiment, the suture-engaging member is positioned distal of a proximal end of the cut-outs. The suture-engaging member can be, for example, a post extending between opposed walls of the inner lumen. In another embodiment, the suture-engaging member can be positioned just proximal to a distal-most end of the elongated body such that the distal end of the elongated body includes a suture-seating groove formed therein and configured to seat at least one suture. The elongate body can also include other features. For example, at least a portion of the inner lumen can have an asymmetrical cross-sectional shape, such as a hexagonal cross-sectional shape, for receiving a driver tool therein. In another embodiment, the distal end of the elongate body can be rounded.

In another embodiment, a suture anchor is provided having a threaded, cannulated body with proximal and distal ends. The distal end can include opposed cut-outs formed in opposed sidewalls thereof and a suture-engaging member extending between the opposed sidewalls and adjacent to the opposed cut-outs such that a suture can extend around the suture-engaging member and trailing ends of the suture can extend through the body. In an exemplary embodiment, the suture-engaging member extends substantially perpendicular to a longitudinal axis of the body. The device can also include a suture disposed around the suture-engaging member and having trailing ends extending through the body.

In yet another embodiment, an apparatus for anchoring tissue to bone is provided and includes a suture anchor having an inner lumen extending between proximal and distal ends thereof. The distal end can include opposed cut-outs formed in opposed sidewalls thereof and a suture-engaging member extending between the opposed sidewalls and adjacent to the opposed cut-outs such that a suture can extend around the suture-engaging member and trailing ends of the suture can extend through the inner lumen of the suture anchor. The apparatus can also include a driver having an elongate shaft and a distal end adapted to be received within and to engage a proximal portion of the inner lumen of the suture anchor. In an exemplary embodiment, the elongate shaft includes an inner lumen extending therethrough for receiving a suture extending through the inner lumen of the suture anchor. A distal end of the elongate shaft can include opposed cut-outs formed therein for allowing a suture extending from the suture anchor to extend externally along the elongate shaft of the driver. In other embodiments, the distal end of the elongate shaft can include a hexagonal cross-sectional shape, and at least a proximal portion of the inner lumen the suture anchor can have a complementary hexagonal cross-sectional shape.

Methods for anchoring suture to bone are also provided. In one exemplary embodiment, the method can include coupling a suture to a suture anchor such that the suture extends around a suture-engaging member formed in a distal end of the suture anchor and trailing ends of the suture extend through an inner lumen extending through the suture anchor. A driver can be inserted into the proximal end of the suture anchor, and the trailing ends of the suture anchor can extend through an inner lumen formed in the driver. The driver can then be actuated to insert the suture anchor into bone to anchor the suture to the bone. While the suture can have various configurations, in one embodiment the suture can include first and second suture strands that extend around the suture-engaging member and that have trailing ends that extend through the inner lumen of the suture anchor and through the inner lumen of the driver. In other aspects, the suture anchor can include threads formed thereon and the driver can be rotated to drive the suture anchor into bone. In an exemplary embodiment, the threads extend from a proximal end of the suture anchor to a distal end of the suture anchor such that the suture anchor is fully threaded into bone.

In yet another embodiment, a suture anchor is provided having an elongate body with proximal and distal ends and an inner lumen extending therethrough. At least one bone-engaging surface feature can be formed on an external surface thereof for engaging bone. The suture anchor can also include a rotatable member extending between opposed sidewalls of the inner lumen and adapted to rotate relative to the elongate body. In one embodiment, the rotatable member can be disposed adjacent the distal end of the elongate body, and it can extend substantially perpendicular to a longitudinal axis of the suture anchor. The rotatable member can be, for example, a post extending between opposed walls of the inner lumen. In another embodiment, the elongate body can include cut-outs formed in opposed sidewalls thereof, extending proximally from the distal end of the elongate body, and in communication with the inner lumen. The rotatable member can be positioned distal of a proximal end of the cut-outs. In another embodiment, the rotatable member can be positioned just proximal to a distal-most end of the elongated body such that the distal end of the elongated body includes a suture-seating groove formed therein and configured to seat at least one suture. The device can also include a suture disposed around the rotatable member and having trailing ends extending through the suture anchor.

In other aspects, an apparatus for anchoring tissue to bone is provided and includes a suture anchor having at least one surface feature formed on an external surface thereof and adapted to engage bone, an inner lumen extending therethrough between proximal and distal ends thereof, and a rotatable member extending across opposed sidewalls of the inner lumen such that a suture can extend around the rotatable member and trailing ends of the suture can extend through the inner lumen of the suture anchor. The apparatus can also include a driver having an elongate shaft and a distal end adapted to be received within and to engage a proximal portion of the inner lumen of the suture anchor.

Exemplary methods for anchoring suture to bone are also provided, and in one embodiment the method can include coupling a suture to a suture anchor such that the suture extends around a rotatable member rotatably disposed within in a distal end of the suture anchor and trailing ends of the suture extend through an inner lumen extending through the suture anchor. A driver can be inserted into the proximal end of the suture anchor, and the driver can be actuated to insert the suture anchor into bone and thereby anchor the suture to the bone. The method can also include pulling one of the trailing ends of the suture to cause the rotatable member to rotate. In one embodiment, the driver can be removed from the suture anchor prior to pulling one of the trailing end of the suture. In an exemplary embodiment, the suture can include a wire attached thereto and pulling the suture can include pulling the wire. In other embodiments, a second suture can be coupled to the wire such that pulling the wire pulls both sutures around the rotatable member and through the inner lumen of the suture anchor.

In yet another embodiment, a suture anchoring system is provided and includes a suture anchor having an inner lumen extending therethrough and a suture-engaging member extending across opposed sidewalls of the inner lumen, and at least one suture having a terminal end that is coupled to at least one wire extending through the inner lumen of the suture anchor and around the suture-engaging member. In an exemplary embodiment, the wire(s) has a diameter that is less than a diameter of the suture(s) coupled thereto. The wire(s) can be connected to the suture(s) using various techniques, such as threading the wire(s) through the terminal end of the suture (s), looping the wire(s) around the terminal end of the suture (s), welding the wire(s) to the terminal end of the suture(s), mating the wire to the terminal end of the at least one suture using a crimp band, and winding a coiled portion of the wire(s) around the terminal end of the suture(s). The suture anchoring system can also include a driver having a distal end adapted to extend into and engage the inner lumen of the suture anchor. The wire(s) can include a first terminal end coupled to the terminal end of the sutures(s), and a second terminal end coupled to the driver.

In yet another embodiment, a suture anchoring system is provided having a threaded, cannulated suture anchor with proximal and distal ends, and a suture-engaging member disposed within a distal end of the suture anchor, and at least one suture having a terminal end that is coupled to a wire extending through the suture anchor and extending around the suture-engaging member. The system can also include a driver having a distal end adapted to extend into and engage the a proximal end of the suture anchor.

In other aspects, a method for anchoring suture to bone is provided and includes coupling a wire to a suture anchor such that the wire extends around a suture-engaging member extending across opposed sidewalls of an inner lumen of the suture anchor and first and second terminal ends of the wire extend through the inner lumen of the suture anchor, inserting the suture anchor into bone, and pulling the first terminal end of the wire to pull at least one suture strand coupled to the second terminal end of the wire through the inner lumen of the suture anchor and around the suture-engaging member. In one embodiment, the wire can be coupled to first and second suture strands such that pulling the first terminal end of the wire pulls the first and second suture strands through the inner lumen of the suture anchor and around the suture-engaging member. Alternatively, the wire can be coupled to a driver that is inserted into the inner lumen of the suture anchor, and that is actuated to drive the suture anchor into bone. Removing the driver from the suture anchor can be effective to pull the wires. The method can also include injecting a material through the inner lumen of the driver and into the inner lumen of the suture anchor. The material can be, for example, a bone-growth promoting material, a sealant, an adhesive, and combinations thereof. The method can also include attaching the suture(s) to tissue to anchor the tissue to the bone.

BRIEF DESCRIPTION OF THE DRAWINGS

The invention will be more fully understood from the following detailed description taken in conjunction with the accompanying drawings, in which:

FIG. 11A is a cross-sectional view of the suture anchor of FIG. 1A having a wire extending therethrough and coupled to a distal end of a driver;

FIG. 11B is a cross-sectional view of the suture anchor of FIG. 1A having a wire extending therethrough and coupled to a proximal end of a driver;

FIG. 12A is a cross-sectional view of the suture anchor of FIG. 1A, showing one technique for coupling two sutures thereto;

FIG. 12B is a cross-sectional view of the suture anchor of FIG. 1A, showing another technique for coupling two sutures thereto;

FIG. 12C is a cross-sectional view of the suture anchor of FIG. 1A, showing a technique for coupling a suture thereto; and FIG. 12D is a cross-sectional view of the suture anchor of FIG. 1A, showing yet another technique for coupling a suture thereto.

DETAILED DESCRIPTION OF THE INVENTION

Certain exemplary embodiments will now be described to provide an overall understanding of the principles of the structure, function, manufacture, and use of the devices and methods disclosed herein. One or more examples of these embodiments are illustrated in the accompanying drawings. Those of ordinary skill in the art will understand that the devices and methods specifically described herein and illustrated in the accompanying drawings are non-limiting exemplary embodiments and that the scope of the present invention is defined solely by the claims. The features illustrated or described in connection with one exemplary embodiment may be combined with the features of other embodiments. Such modifications and variations are intended to be included within the scope of the present invention.

The present invention generally provides methods and devices for anchoring suture to bone. In an exemplary embodiment, a cannulated suture anchor is provided and it includes a suture-engaging member formed therein and configured to receive a suture therearound such that trailing ends of the suture can extend through the suture anchor. The use of a cannulated suture anchor also allows a driver to be inserted into the inner lumen of the suture anchor for driving the suture anchor into bone. Such a configuration will allow the torque strength of the suture anchor to be maximized due to the increased engagement between the suture anchor and the driver. This in turn will allow the suture anchor to be formed from a broad range of materials, including bioabsorbable and/or osteoconductive materials. The use of a cannulated suture anchor will also eliminate the need for a driver head formed on the suture anchor, and as a result the entire length of the suture anchor can be configured to be fully engaged through the thickness of hard cortical bone, thus optimizing cortical bone fixation to provide a more secure fixation. This will help prevent migration of the suture anchor. A cannulated suture anchor is also particularly advantageous as it allows materials, such as bone-growth promoting materials, sealants, adhesives, etc., to be introduced therein to facilitate fixation. The present invention also provides exemplary sutures and drivers that can be used with the various methods and devices disclosed herein, or with other methods and devices known in the art. A person skilled in the art will appreciate that, while methods and devices are disclosed herein for anchoring soft tissue to bone, the methods and devices can be used in a variety of other medical procedures for anchoring various objects to one another.

Figure 1A:
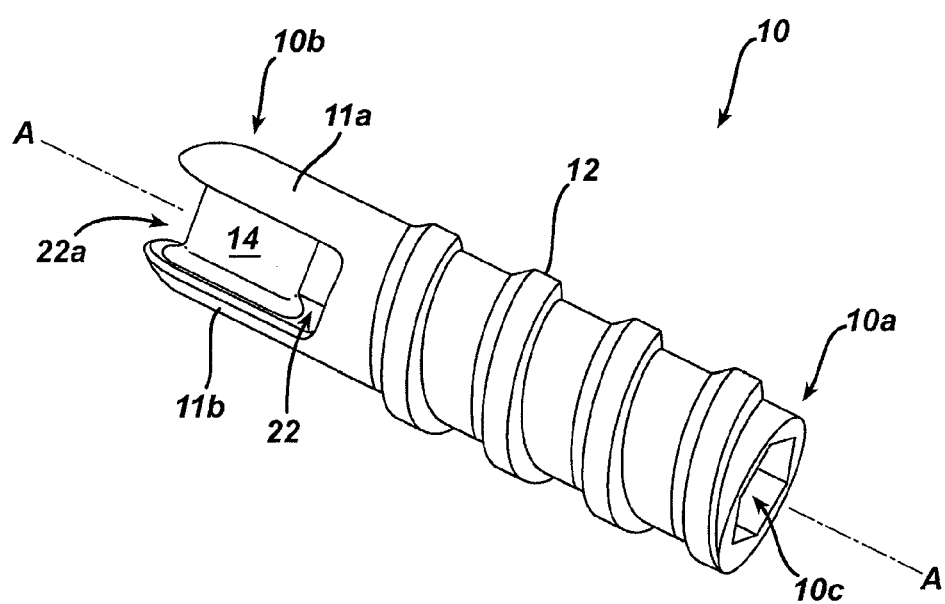
FIG. 1A is a perspective view of one embodiment of a cannulated suture anchor.
Figure 1B:
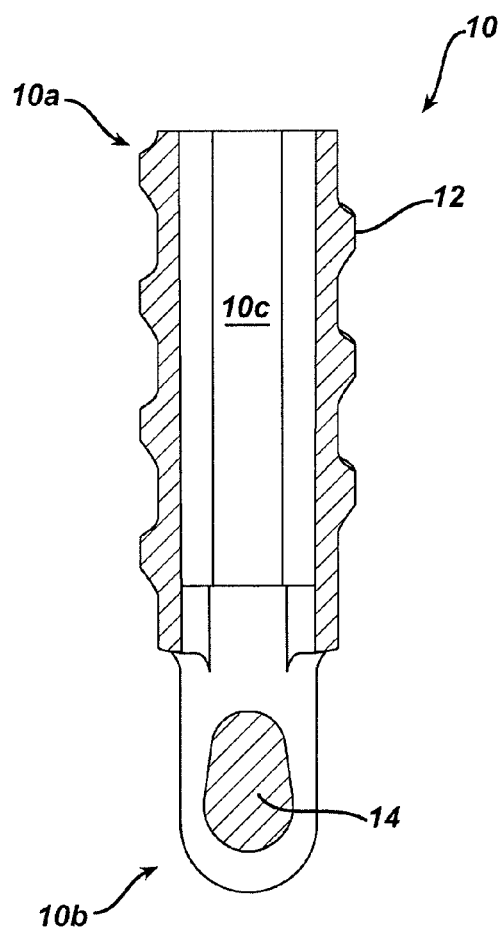
FIG. 1B is a cross-sectional view of the suture anchor of FIG. 1A.
Figure 1C:
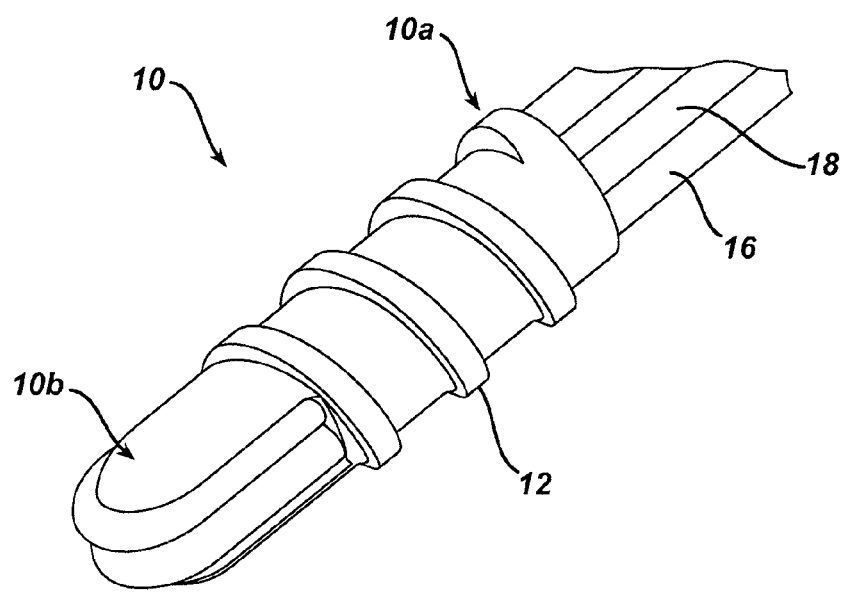
FIG. 1C is a perspective view of the suture anchor of FIG. 1A having first and second sutures coupled thereto.

FIGS. 1A-1C illustrate one exemplary embodiment of a cannulated suture anchor 10 for anchoring soft tissue to bone. As shown, the suture anchor 10 is in the form of a generally elongate body having proximal and distal ends 10a, 10b with an inner lumen 10c extending therethrough. At least one bone-engaging surface feature 12 can be formed on at least a portion of an external surface thereof for engaging bone. The suture anchor 10 also includes a suture-engaging member 14 disposed within the inner lumen 10c adjacent to the distal end 10b of the suture anchor 10. As shown in FIG. 1C, the suture-engaging member 14 is adapted to receive one or more sutures (two sutures 16, 18 are shown) therearound such that the suture(s) can extend around the suture-engaging member 14 and trailing ends of the suture(s) can extend through the inner lumen 10c and out of the proximal end 10a of the suture anchor 10.

The body of the suture anchor 10 can have a variety of configurations, shapes, and sizes. In an exemplary embodiment, the body is configured to be implanted within a bone tunnel formed in bone, and more preferably it has a size and shape that allows it to be fully engaged through the thickness of the cortical bone. In the illustrated embodiment the body has a generally elongate cylindrical shape with a blunt or rounded distal end 10b to facilitate introduction into a bone tunnel. The proximal end 10a of the body is head-free, as the cannulated configuration of the body allows a driver to be inserted into the inner lumen 10c to drive the suture anchor 10 into bone. As indicated above, the suture anchor 10 can also include one or more bone-engaging surface features formed thereon and adapted to engage bone. While various surface features can be used, such as teeth, ridges, protrusions, etc., in an exemplary embodiment the body can include one or more threads extending therearound. In the illustrated embodiment a single thread extends around the body from the proximal end 10a and it terminates proximal to the distal end 10b. The particular location at which the thread terminates can vary depending on the particular configuration of the suture anchor 10. As will be discussed in more detail below, the illustrated suture anchor 10 can include opposed cut-outs formed in the distal end thereof and the thread can terminate just proximal to the proximal end of the cut-outs.

The suture anchor 10 can also be formed from a variety of materials. In an exemplary embodiment, the material has physical properties that are sufficient to allow a driver to be inserted into the inner lumen 10c of the suture anchor 10 and to be used to drive the suture anchor 10 into bone without damaging the suture anchor 10. The properties of the material will of course depend on the particular configuration of the suture anchor 10. For example, the inner lumen 10c of the suture anchor 10 can have a length that maximizes the torque strength of the suture anchor 10 as well as the amount of surface contact between a driver and the suture anchor 10, thus allowing weaker materials, such as bioabsorbable and/or osteoconductive materials to be used. A person skilled in the art will appreciate that a variety of other materials, including plastics and metals, can be used to form the suture anchor 10.

As previously indicated above, the suture anchor 10 can also include a suture-engaging member 14 formed therein. The suture-engaging member 14 can have a variety of configurations, but in an exemplary embodiment it is adapted to engage one or more sutures that extend through the inner lumen 10c of the suture anchor 10. As shown in FIGS. 1A and 1B, the suture-engaging member 14 is in the form of a post that extends transversely across the inner lumen 10c and between opposed inner sidewalls of the suture anchor 10. The angular orientation of the suture-engaging member 14 relative to a longitudinal axis A of the inner lumen 10c can vary, but in an exemplary embodiment the suture-engaging member 14 extends substantially perpendicular to the longitudinal axis A of the inner lumen 10c. The location of the suture-engaging member 14 can also vary, but in an exemplary embodiment the suture-engaging member 14 is positioned at or adjacent to the distal end 10b of the suture anchor 10. In the embodiment shown in FIGS. 1A and 1B, the suture-engaging member 14 is located just proximal to the distal-most end 10b of the suture anchor 10 so as to form a suture-seating groove 22a in the distal-most end of the suture anchor 10. This recessed configuration of the suture-engaging member 14 can allow a suture(s) disposed around the suture-engaging member 14 to sit flush or sub-flush with the distal end 10b of the suture anchor 10 such that the suture(s) will not interfere with insertion of the suture anchor 10 into bone. A person skilled in the art will appreciate that the suture-engaging member 14 can be integrally formed with the suture anchor 10, i.e., the suture anchor 10 and suture-engaging member 14 can be molded as a single unit or formed from a single piece of material, or the suture-engaging member 14 can be fixedly or removably mated to the suture anchor 10.

As further shown in FIGS. 1A-1C, in order to facilitate positioning of a suture(s) around the suture-engaging member 14, the suture anchor 10 can include one or more cut-outs formed in a sidewall thereof adjacent to the suture-engaging member 14. As best shown in FIG. 1A, in an exemplary embodiment the suture anchor 10 includes a cut-out 22 that begins just proximal to the location of the suture-engaging member 14, and that extends around the distal end 10b of the suture anchor 10 such that the suture anchor 10 includes opposed cut-outs or openings formed on opposed sides of the suture-engaging member 14 and a distal cut-out that defines the suture-seating groove 22a for seating a suture(s). The cut-out 22 can also define opposed distal arms 11a, 11b on the suture anchor 10 that are spaced a distance apart from one another and that have the suture-engaging member 14 extending therebetween.

A person skilled in the art will appreciate that the particular location and configuration of the cut-out 22 can define the particular location and configuration of the suture-engaging member 14, as the cut-out 22 can be formed during manufacturing to create the suture-engaging member 14. Alternatively, the particular location and configuration of the opposed arms 11a, 11b can define the particular location and configuration of the cut-out 22, as the shape and size of the arms 11a, 11b defines the shape and size of the cut-out 22. The location of the suture-engaging member 14 relative to the cut-out 22 and/or arms 11a, 11b will also define the configuration of the distal end of the suture anchor 10, and whether the suture anchor 10 includes a distal groove 22a for seating a suture(s).

As further shown in FIGS. 1A and 1B, the inner lumen 10c of the suture anchor 10 can be adapted to receive a driver therein for driving the suture anchor 10 into bone. While various techniques can be used to facilitate engagement between the inner lumen 10c and a driver mechanism, in an exemplary embodiment the inner lumen 10c, or at least a portion thereof, has an asymmetrical shape that complements a corresponding asymmetrical shape of a driver. The asymmetrical portion preferably extends along a substantial length of the inner lumen 10c so as to maximum surface contact between a driver and the suture anchor. By way of non-limiting example, FIGS. 1A and 1B illustrate a hexagonal cross-sectional shape formed in a proximal portion of the inner lumen 10c for receiving a driver having a corresponding hexagonal drive tip, as will be discussed in more detail below. The hexagonal cross-section extends from the proximal-most end 10a of the suture anchor 10 and terminates just proximal to the proximal end of the cut-out 22.

In another embodiment, rather than having a fixed suture-engaging member 14, the suture anchor can include a suture-engaging member that is rotatably disposed therein. Such a configuration will allow for suture slidability, providing a pulley system to facilitate longitudinal movement of a suture through the inner lumen of the suture anchor. In particular, one or more terminal ends of one or more sutures disposed around the suture-engaging member can be pulled to slide the suture(s) longitudinally within the inner lumen of the suture anchor, and the suture-engaging member can rotate to facilitate such longitudinal movement.

Figure 2:
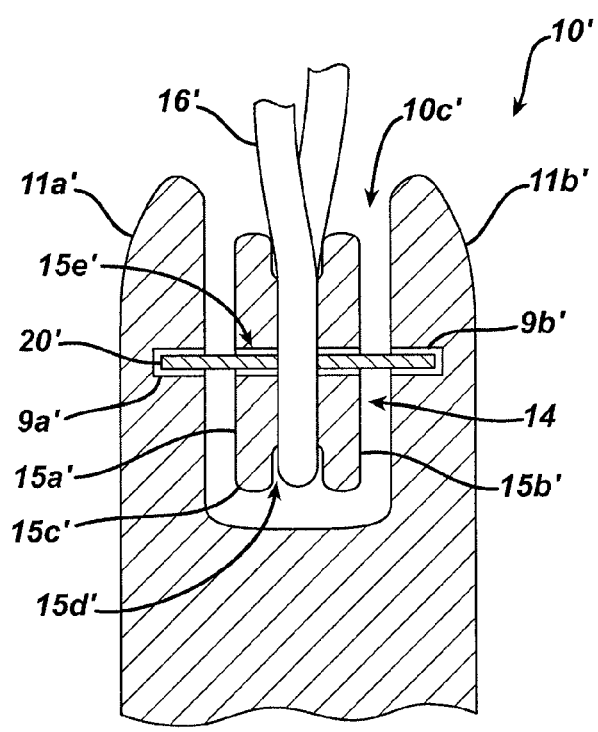
FIG. 2 is a cross-sectional view of a distal portion of a suture anchor having a rotatable suture-engaging member according to another embodiment of the present invention.

While the rotatable suture-engaging member can have a variety of configurations, FIG. 2 illustrates one exemplary embodiment of a rotatable suture-engaging member 14' that is disposed within an inner lumen 10c' of a suture anchor 10'. As shown, the suture-engaging member 14' is in the form of a generally cylindrical body having opposed sidewalls 15a', 15b' and a continuously curved outer wall 15c' extending therearound and between the opposed sidewalls 15a', 15b'. A groove 15d' is formed in the outer wall 15c' for seating one or more sutures, such as suture 16'. The suture-engaging member 14' also includes a bore 15e' extending therethrough between the opposed sidewalls 15a', 15b' for receiving a pin member 20' that allows the suture-engaging member 14' to rotate therearound. The pin member 20' can extend into opposed bores or openings 9a', 9b' formed in an inner surface of the opposed arms 11a', 11b' of the suture anchor 10. A person skilled in the art will appreciate that a variety of other techniques can be used to rotatably mate the suture-engaging member 14' to the suture anchor 10'. Alternatively, other techniques can be used to facilitate suture slidability, such as a lubricious coating applied to the suture engaging member.

Figure 3A:
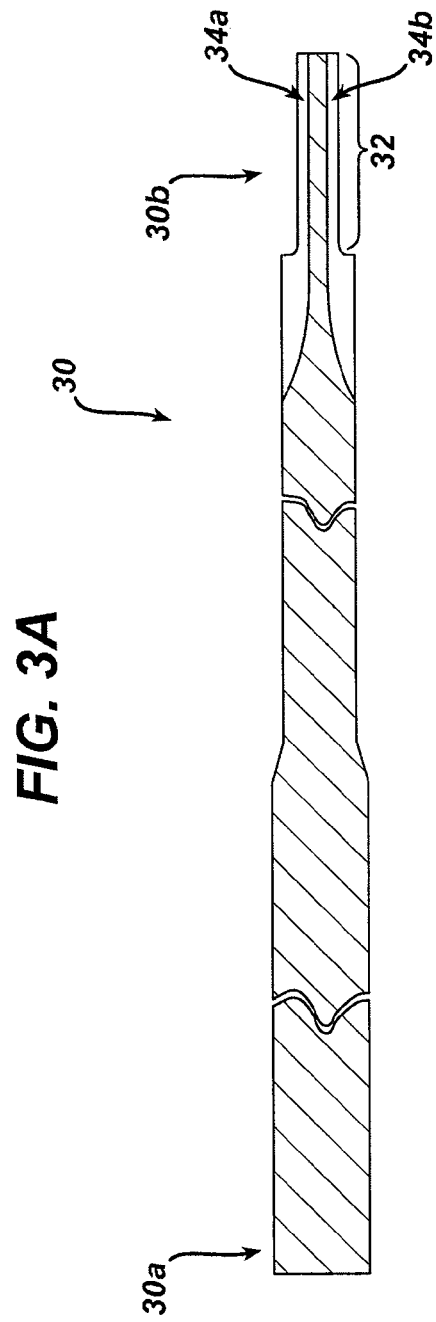
FIG. 3A is a cross-sectional view of one embodiment of a driver tool.
Figure 3B:
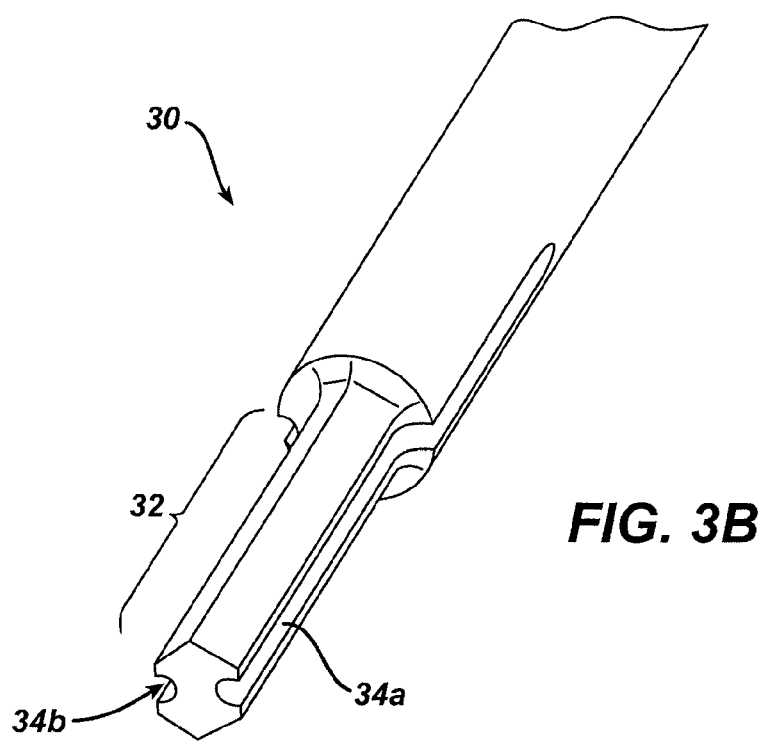
FIG. 3B is a perspective view of the driver tool of FIG. 3A.

As previously indicated, the suture anchors disclosed herein can be cannulated for receiving a driver. While various drivers known in the art can be used, FIGS. 3A and 3B illustrate one exemplary embodiment of a driver 30 for driving a suture anchor into bone. In this embodiment, the driver 30 is adapted to allow the terminal ends of a suture(s) extending through the suture anchor to extend along an external surface thereof. As shown, the driver 30 is in the form of a generally elongate shaft having proximal and distal ends 30a, 30b. While not shown, the proximal end 30a can include a handle or other grasping mechanism formed thereon to facilitate grasping and manipulation of the device. The distal end 30b includes a reduced diameter portion or tip 32 that is configured to fit within the inner lumen of a suture anchor, such as lumen 10c of anchor 10. The shape of the tip 32 can vary, but in an exemplary embodiment it has an asymmetrical shape that allows the tip 32 to engage the inner lumen 10c of the anchor 10. In the illustrated embodiment the tip 32 has a generally hexagonal cross-sectional shape that complements the generally hexagonal cross-sectional shape of the inner lumen 10c in the anchor. The length of the tip 32 can also vary, but in an exemplary embodiment the tip 32 has a length that allows it to extend through a substantial portion of the lumen 10c in the anchor 10 so as to maximize surface contact between the tip 32 and the anchor 10. For example, the length 32 can correspond to a length of the hexagonal portion of the inner lumen 10c in the anchor. A person skilled in the art will appreciate that the tip 32 can have a variety of other shapes, sizes, and configurations.

As further shown in FIGS. 3A and 3B, the tip can also include one or more suture-receiving recesses or grooves formed therein and extending longitudinally along the length of the tip 32 for seating one or more sutures. In the illustrated embodiment first and second opposed suture-receiving grooves 34a, 34b are formed in the tip 32 and extend along the length thereof. The grooves 34a, 34b can also optionally extend a distance beyond a proximal end of the tip 32, as shown, or along the entire length of the driver 30, so as to further prevent the suture(s) from interfering with insertion of the suture anchor 10.

Figure 3C:
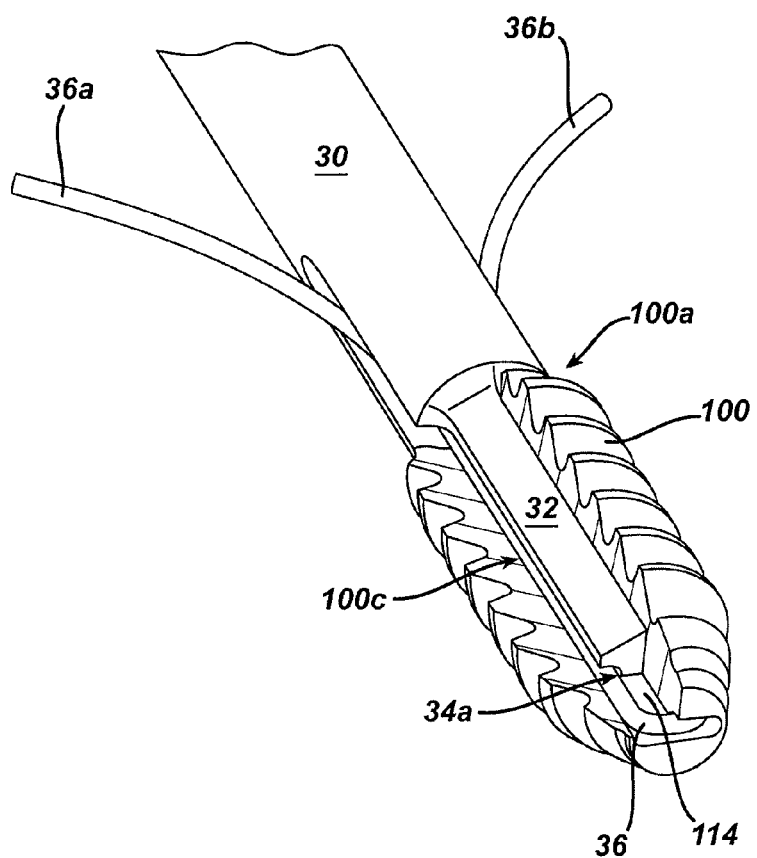
FIG. 3C is a perspective view of the driver tool of FIG. 3A coupled to a suture anchor and having a suture extending therethrough.

FIG. 3C illustrates a cut-away view of the driver 30 disposed within a suture anchor 100 that is similar to suture anchor 10. As shown, a suture 36 is disposed through the lumen 100c of the suture anchor 100 and around the suture-engaging member 114 such that first and second trailing ends 36a, 36b of the suture 36 extend proximally from the proximal end 100a of the suture anchor 100. In order to allow the distal tip 32 of the driver 30 to fit within and engage the inner lumen 100c of the suture anchor 100, the opposed ends of the suture 36 extending from the suture-engaging member 14 can be seated within the opposed grooves (only one groove 34a is shown) formed in the tip 32.

Figure 4A:
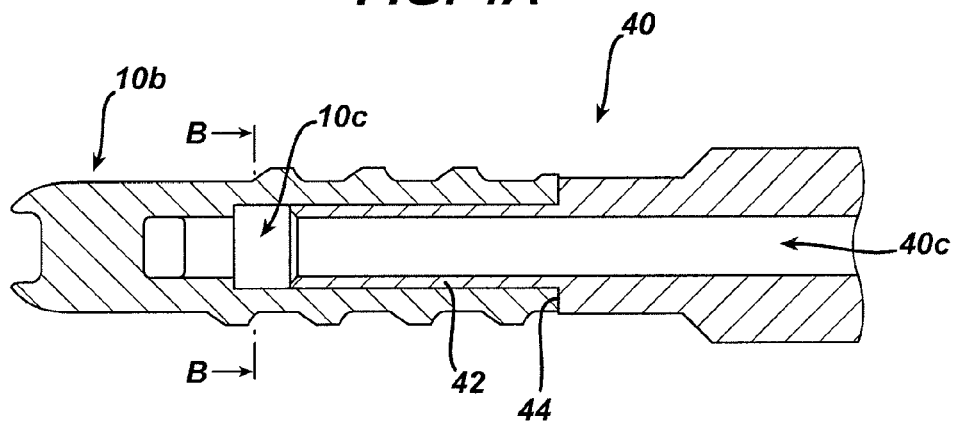
FIG. 4A is a cross-sectional view of the suture anchor of FIG. 1A having another embodiment of a driver tool disposed therein.
Figure 4B:
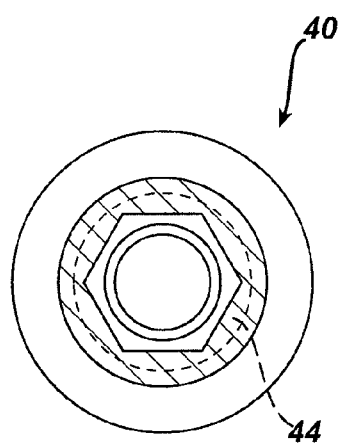
FIG. 4B is a cross-sectional view of the driver tool of FIG. 4A taken across line B-B.

In another embodiment, as shown in FIGS. 4A and 4B, the driver 40 can be cannulated to allow the terminal ends of a suture(s) extending through the suture anchor to extend therethrough, rather than extending external to the driver. In particular, the driver 40 is similar to driver 30, except that the driver 40 includes an inner lumen 40c extending through the entire length thereof for receiving one or more sutures, rather than having suture-receiving grooves formed in the distal tip. FIG. 4A illustrates the distal tip 42 of the driver 40 disposed within and engaging the inner lumen 10c of suture anchor 10. As shown, the diameter of the remainder of the driver 40 as compared to the reduced-diameter of the distal tip 42 can provide a stop surface 44 that limits the depth of insertion of the distal tip 42 into the inner lumen 10c of the anchor 10. As previously discussed, the length of the distal tip 42, and thus the depth of insertion of the tip 42 into the inner lumen 10c of the anchor 10, can vary depending on the size and shape of the suture anchor 10. In an exemplary embodiment, the tip 42 is configured to be inserted into a substantial portion of the inner lumen 10c so as to maximum surface contact between the driver 40 and the suture anchor 10. In other embodiments, the cannulated driver 40 can also optionally be used to allow other materials, such as bone-growth promoting materials, adhesives, biologics, and other injectable materials, to be introduced through the driver and into the suture anchor.

As previously indicated, the suture anchors and drivers disclosed herein can be configured for use with one or more sutures. The particular quantity of sutures used with a suture anchor and driver can depend on the size of the suture anchor and the driver, and in particular on the diameter of the inner lumen of the suture anchor and the size of the suture-engaging groove formed in the driver (for driver 30) or the diameter of the lumen in the driver (for driver 40). For example, where the suture anchor has a relatively small inner lumen, the driver will necessarily have a relatively small diameter and thus small suture-engaging grooves (for driver 30) or a small inner lumen (for driver 40). It may therefore only be possible to use a single suture that is positioned around the suture-engaging member on the suture anchor, and that has two trailing ends extending through the suture-receiving grooves in the driver (for driver 30) or through the inner lumen in the driver (for driver 40). While a single suture can be sufficient to anchor tissue to bone, it is preferred to use more than one, and more preferably two, sutures. Thus, rather than increasing a size of the suture anchor and/or the driver, the present invention provides various exemplary techniques for utilizing two sutures with a suture anchor and driver that are configured to seat only one suture. This is particularly advantageous as the suture anchor can be sized to be fully disposed within cortical bone, while the diameter of the inner lumen of the suture anchor and of the distal tip of the driver are maximized to increase the torque failure rating. This also enables the anchor to be made from a broad range of materials, including brittle or weaker materials such as those previously disclosed herein.

In one embodiment, one or more sutures can be coupled to a thin wire, thread, string, small diameter suture, etc. (hereinafter generically referred to as a wire), and the wire can extend through the suture-receiving grooves or inner lumen in the driver. Since the wire will have a diameter that is significantly smaller than a diameter of the suture, one or more wires can be used in place of the trailing end of one or mores sutures, thus allowing multiple sutures to be used. This is illustrated, by way of non-limiting example, in FIGS. 5A and 5B.

Figure 5A:
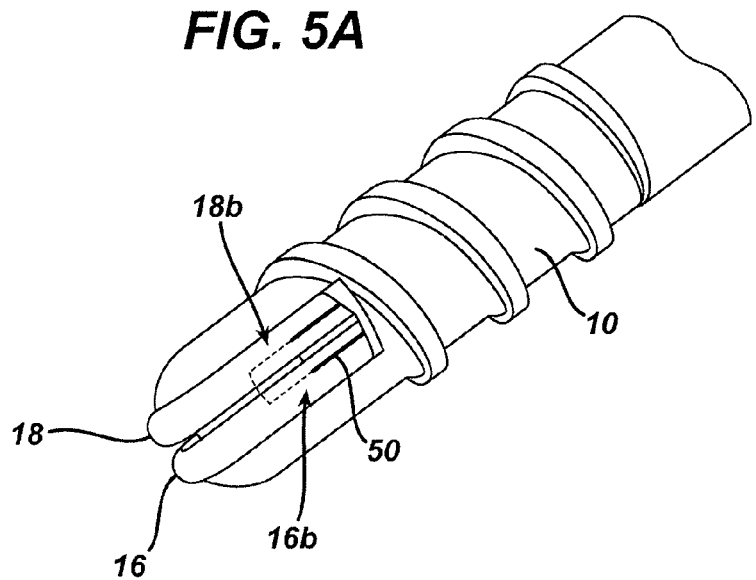
FIG. 5A is a perspective view of the suture anchor of FIG. 1A having first and second sutures coupled thereto, showing a wire coupled to the terminal end of each suture.

FIG. 5A illustrates a suture anchor 10 having first and second sutures 16, 18 extending therethrough and around the suture-engaging member (not shown). Since all four trailing ends (i.e., the ends extending from the suture-engaging member) of the sutures 16, 18 will not fit within the suture-receiving grooves in driver 30 (not shown) or through the inner lumen of driver 40 (not shown), only one trailing end of each suture 16, 18 can extend through the driver and the terminal end 16b, 18b of the other trailing end of each suture 16, 18 can be positioned just distal to the proximal end of the cut-out 22. A wire 50 can be mated to each terminal end 16b, 18b and the wire can extend proximally from the terminal ends 16b, 18b and through the driver. In use, once the suture anchor 10 is implanted in bone, the driver can be removed and the wire 50 can be pulled to pull the terminal ends 16b, 18b of the sutures 16, 18 proximally around the suture-engaging member and through the suture anchor 10. The terminal ends can thereafter be used to secure tissue to bone. A person skilled in the art will appreciate that the sutures can remain external to the driver and anchor while only the wire(s) extend through the driver and anchor, and the sutures can be pulled into the anchor after placement of the suture anchor.

Figure 5B:
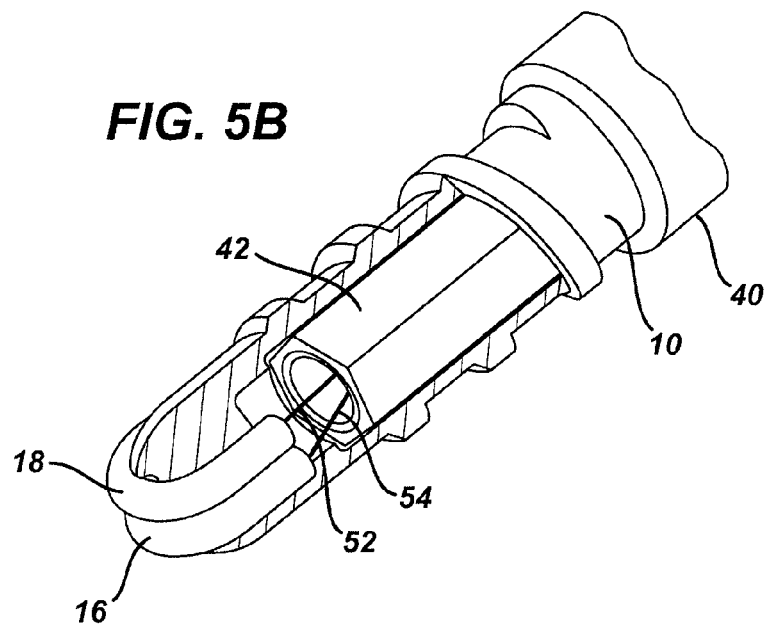
FIG. 5B is a perspective view of the suture anchor of FIG. 1A having first and second sutures coupled thereto, showing first and second wires coupled to the terminal ends of the first and second sutures, respectively.
Figure 5C:
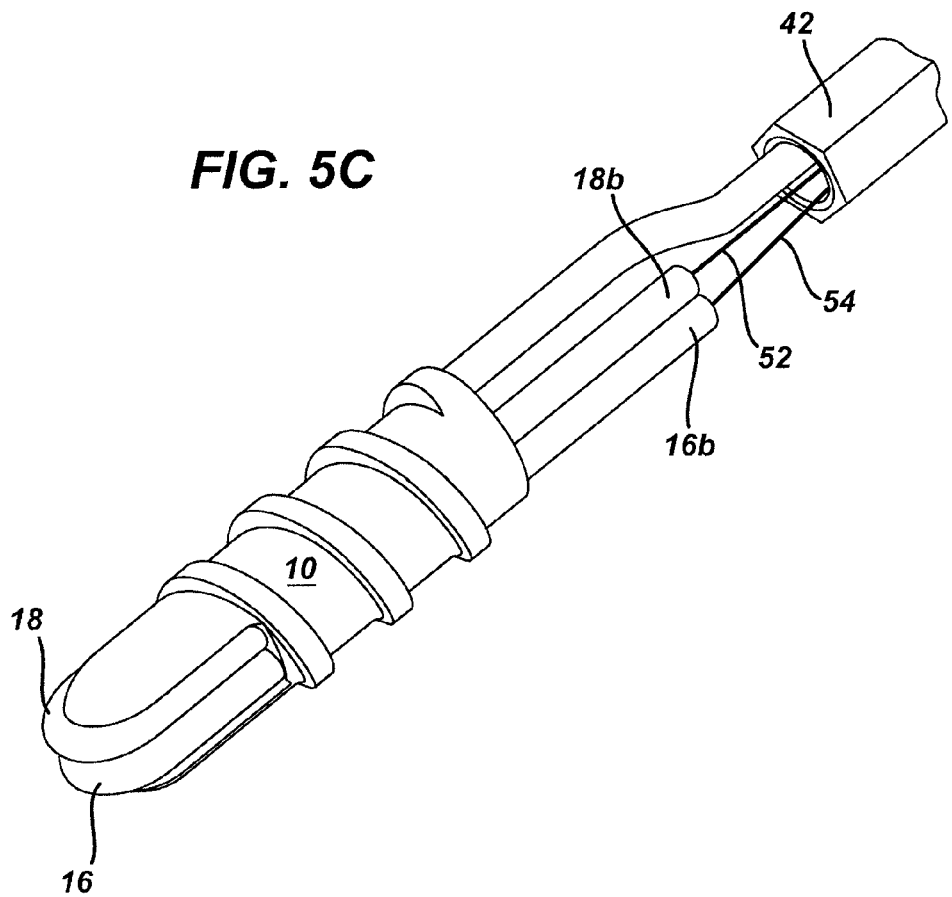
FIG. 5C is a perspective view of the suture anchor and sutures of FIG. 5B, showing the wires pulling the sutures through the suture anchor.
Figure 6:
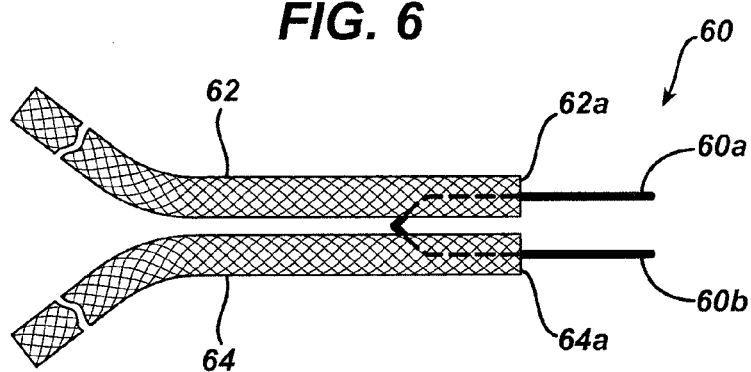
FIG. 6 is a side view of a technique for threading a wire to a suture.
Figure 7:
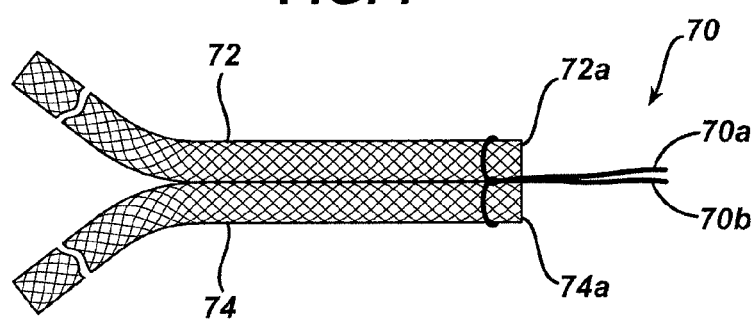
FIG. 7 is a side view of a technique for tying a wire to a suture.
Figure 8:
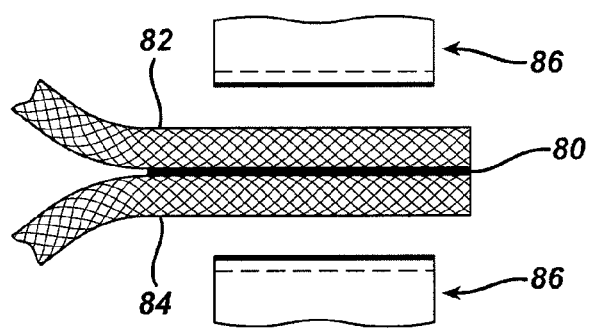
FIG. 8 is a side view of a technique for welding a wire to a suture.
Figure 9:
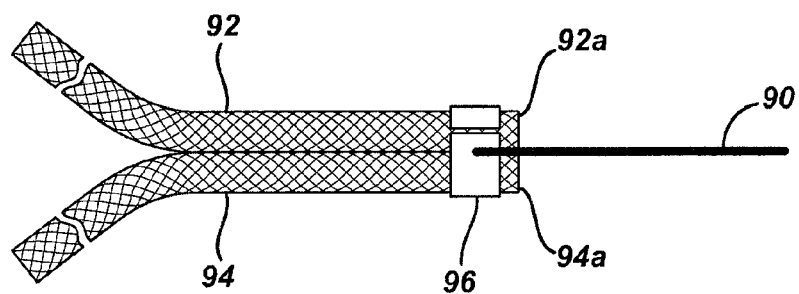
FIG. 9 is a side view of a technique for mating a wire to a suture using a clamp.
Figure 10:
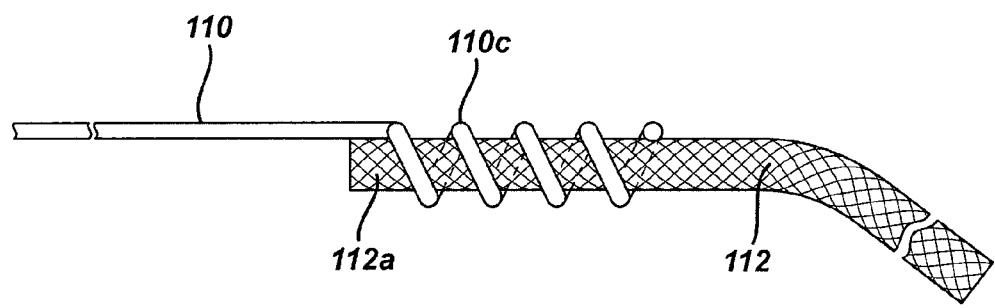
FIG. 10 is a side view of a technique for mating a wire to a suture using a coil formed on the wire.

In another embodiment, shown in FIG. 5B, the terminal ends 16b, 18b of the sutures 16, 18 can be mated to separate wires 52, 54 that extend through the inner lumen of the driver. FIG. 5B illustrates a partially cut-away view of the suture anchor 10, showing the distal tip 42 of driver 40 disposed therein and having the wires 52, 54 extending therethrough. As with the embodiment shown in FIG. 5A, one trailing end of each suture 16, 18 and the wires 52, 54 can extend through the driver 40, thus allowing two sutures 16, 18 to be used with the anchor 10. After the suture anchor is implanted, the driver 40 can be removed and the wires 52, 54 can be used to pull the terminal ends 16b, 18b of the sutures 16, 18 around the suture-engaging member in a proximal direction, as shown in FIG. 5C. A person skilled in the art will appreciate that while FIG. 5B illustrates driver 40, the wires can be used with driver 30, or with any other driver known in the art.

The use of wires extending through a cannulated driver can also be advantageous in that various materials, such as those previously discussed, can be introduced through the inner lumen of the driver with the wires in place. For example, an adhesive can be injected through the inner lumen of the driver prior to pulling the terminal ends 16b, 18b of the sutures 16, 18 proximally, thus allowing the suture 16, 18 to be secured to the suture anchor 10.

A person skilled in the art will appreciate that a variety of techniques can be used to mate a wire to one or more sutures. By way of non-limiting example, FIGS. 6-10 illustrate various exemplary mating techniques. In the embodiment shown in FIG. 6, a single wire 60 is threaded through a terminal end 62a of a first suture 62 and then is threaded back through a terminal end 64a of a second suture 64 such that trailing ends 60a, 60b of the wire 60 extend from the terminal ends 62a, 64a of the sutures 62, 64. In another embodiment, shown in FIG. 7, the wire 70 is looped or knotted around the terminal ends 72a, 74a of two sutures 72, 74 such that trailing ends 70a, 70b of the wire 70 extend from the terminal ends 72a, 74a of the sutures 72, 74. In the embodiment shown in FIG. 8, the wire 80 is positioned between two sutures 82, 84 and it is welded to the sutures 82, 84 using an ultrasonic welder 86, or using other welding techniques known in the art. In another embodiment, shown in FIG. 9, a wire 90 can be attached to a clamp or crimp band 96 that is disposed around and closed to engage the terminal ends 92a, 94a of two sutures 92, 94. In yet another embodiment, shown in FIG. 10, the wire 110 can include a spring or coiled portion 110c formed on a terminal end thereof. The coiled portion 110c can be positioned around the terminal end 112a of a suture 112, and it can be biased to a shape in which the coiled portion 110c engages the suture 112. When the wire 110 is pulled to pull the suture 112, the coiled portion 110c can optionally decrease in diameter to provide a more secure engagement between the wire 110 and the suture 112. A person skilled in the art will appreciate that the aforementioned mating techniques can be used to mate a single wire to one or more sutures, or to mate multiple wires to a single suture. Moreover, a variety of other mating techniques can be used, including adhesives etc.

Figure 11C:
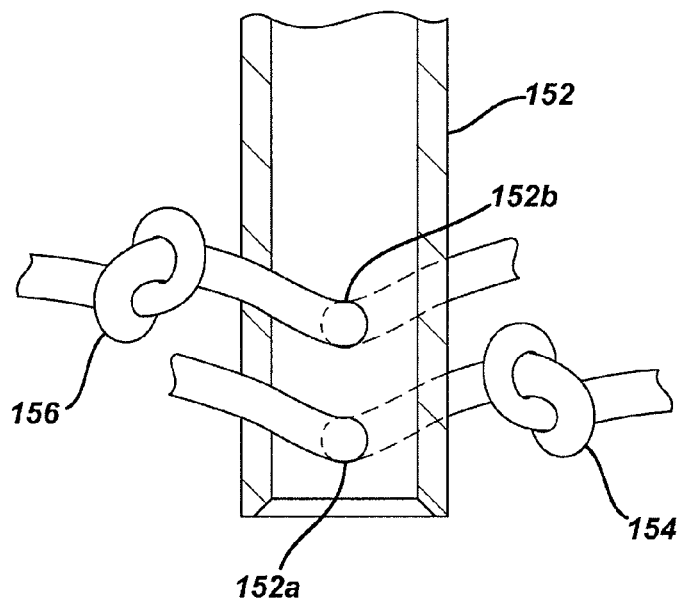
FIG. 11C is a cross-sectional view of a portion of a driver tool, showing a technique for mating a wire thereto.

In another embodiment, one of the trailing ends of a suture or a wire can be mated to the driver. As the driver is removed from the suture anchor, the driver will pull the suture or wire attached thereto around the suture engaging member. This is illustrated in FIGS. 11A and 11B. In the embodiment shown in FIG. 11A, a first end 132a of a wire 132 is attached to a distal end 130d of a driver 130. The second end 132b of the wire 132 extends through the suture anchor 10 and proximally from the driver 130, where it can be coupled to a suture. The wire 132 can be pulled into the suture anchor 10 and around the suture-engaging member 14 as the driver 130 is removed. In another embodiment shown in FIG. 11B, the first end 132a' of the wire 132' can be attached to a proximal end 130p' of the driver 130'. A person skilled in the art will appreciate that the particular attachment location of the wire to the driver can vary. Moreover, a variety of techniques can be used to attach a suture or a wire to a driver. By way of non-limiting example, FIG. 11C illustrates one exemplary embodiment of an attachment technique. As shown, the distal tip 152 of a driver includes first and second bores 152a, 152b formed therein, and the trailing ends of first and second wires 154, 156 are inserted through the bores 152a, 152b. A knot is formed in the terminal end of each wire 154, 156 to retain the wires 154, 156 within the bores 152a, 152b. In use, instead of having four trailing ends of two sutures extending through the driver, only one trailing end of each suture or wire will extend through the driver while the other end will remain attached to the distal tip 152. Alternatively, the trailing ends of two wires can extend through the driver and attach to sutures positioned external to the driver. When the driver is removed, the driver will pull the sutures around the suture-engaging member to allow the trailing ends of the sutures to be used to secure tissue to bone. The knots can be cut or otherwise removed to detach the sutures from the driver.

In other embodiments, shown in FIGS. 12A-12D, various threading techniques can be used to allow two sutures to be used with the suture anchors disclosed herein. FIG. 12A illustrates suture anchor 10 having two sutures 16, 18 extending through the inner lumen 10c of the suture anchor 10 and looped around the suture-engaging member 14. Conversely, one of the sutures, e.g., suture 18, can extend along an external surface of the suture anchor 10, as shown in FIG. 12B. Similarly, a single suture can be used and it can extend through both the inner lumen 10c of the suture anchor 10, as well as along an external surface of the suture anchor 10. This is illustrated in FIG. 12C. As shown, a first trailing end 16a of the suture 16 is positioned along an external surface of the suture anchor 10, and the second trailing end 16b of the suture 16 is threaded around the suture-engaging member 14 and up through the inner lumen 10c, where a first loop is formed. The second trailing end 16b of the suture 16 is then passed back through the inner lumen 10c and positioned to extend externally along the length of the suture anchor 10. While FIG. 12C illustrates both trailing ends 16a, 16b of the suture 16 extending externally along the suture anchor 10, in another embodiment one trailing end can extend externally along the suture anchor 10 while the other trailing end can extend through the inner lumen 10c of the suture anchor 10. This is illustrated in FIG. 12D, which shows the suture 16 having a first trailing end 16a extending through the inner lumen 10c of the suture anchor 10 and proximally beyond the proximal end 10a of the suture anchor 10. The second trailing end 16b is passed through the inner lumen 10, around the suture-engaging member 14, and externally around the suture anchor 10. It is then passed back into the proximal end 10a of the suture anchor and through the inner lumen 10c, where it is positioned around the suture-engaging member 14 and externally along the suture anchor 10. A person skilled in the art will appreciate that a variety of other threading techniques can be used to allow one or more sutures to be used with the various suture anchors and/or drivers disclosed herein.

The present invention also provides exemplary methods for anchoring tissue to bone. While the method is described in connection with attaching soft tissue to bone, the methods and devices disclosed herein can be used in a variety of medical procedures for anchoring one structure to another. In general, a bore is formed in bone of a patient. The diameter of the bore is preferably slightly less than the largest outer diameter of the suture anchor, and the length of the bore it preferably the same as or slightly greater than a length of the suture anchor. The bore will extend fully through the cortical bone to allow the suture anchor to be fully engaged through the thickness of the cortical bone. The bore can also extend into the cancellous bone depending on the length of the suture anchor. One or more sutures (including sutures with wires coupled thereto) can be coupled to the suture anchor using various techniques, as previously discussed herein, and the distal tip of a driver can be inserted into the lumen in the suture anchor. The trailing ends of the suture(s) or wire(s) can extend externally along the driver or they can extend through an inner lumen of the driver. The driver can then be used to insert the suture anchor into the bone tunnel. For example, where the suture anchor includes threads formed thereon, the driver can be rotated to thread the suture anchor into the bone hole. The threads will engage the bone hole thereby preventing removal of the suture anchor. In other embodiments, the driver can be used to tap the bone anchor into the bone hole, and an interference fit, compression fit, and/or surface features, such as ribs or protrusions, formed on the suture anchor can be used to retain the suture anchor within the bone hole. The driver can also optionally be used to impact a threaded suture anchor into the bone hole. The threads can allow for later removal of the suture anchor.

Once the bone anchor is properly anchored within the bone hole, various materials, such as those previously discussed herein, can be introduced through the driver and into or around the suture anchor. The driver can then be removed. Where the suture(s) have wire(s) attached thereto, the wire(s) can be pulled to pull the suture(s) around the suture-engaging member of the suture anchor. If the suture anchor includes a rotatable suture-engaging member, the suture-engaging member will rotate as the suture(s) is pulled therearound. The trailing ends of the suture(s) can then be used to anchor soft tissue to the bone. For example, one or both trailing ends of the suture(s) can be attached to a needle to allow the needle to be used to thread the suture through tissue to be anchor to the bone. The suture(s) can be threaded through tissue either prior to or after insertion of the suture anchor into bone. Once the soft tissue is approximated toward the bone, the trailing ends of the suture(s) can be secured together and the excess trimmed as is typical in these situations to complete the surgery.

One skilled in the art will appreciate further features and advantages of the invention based on the above-described embodiments. Accordingly, the invention is not to be limited by what has been particularly shown and described, except as indicated by the appended claims. All publications and references cited herein are expressly incorporated herein by reference in their entirety.

What is claimed is:

1. An apparatus for anchoring tissue to bone, comprising:
 a suture anchor having an inner lumen extending between proximal and distal ends thereof, the distal end including opposed cut-outs formed in opposed sidewalls thereof and a suture-engaging member positioned in the inner lumen, extending between the opposed sidewalls at an immovably fixed longitudinal position with respect to the opposed cut-outs, and adjacent to the opposed cut-outs such that a suture can extend around the suture-engaging member and trailing ends of the suture can extend through the inner lumen of the suture anchor, wherein the suture-engaging member does not extend distally beyond a distal-most end of the suture anchor; and
 a driver having an elongate shaft and a distal end adapted to be advanced distally into the inner lumen of the suture anchor through the proximal end thereof to be received within and to engage a proximal portion of the inner lumen of the suture anchor,
 wherein, when the distal end of the driver is being advanced distally within the inner lumen of the suture anchor, the distal end of the driver cannot extend distally beyond the distal-most end of the suture anchor; and
 wherein, when the distal end of the driver engages the proximal portion of the inner lumen of the suture anchor, the driver is adapted to be rotated so as to rotate the suture anchor relative to bone so as to drive the suture anchor into the bone.

2. The apparatus of claim 1, wherein the elongate shaft includes an inner lumen extending therethrough for receiving a suture extending through the inner lumen of the suture anchor.

3. The apparatus of claim 2, wherein, when the distal end of the driver is received within and engages the proximal portion of the inner lumen of the suture anchor, the suture anchor and the driver are configured such that an injectable material can be introduced through the inner lumen of the driver and into the inner lumen of the suture anchor.

4. The apparatus of claim 3, wherein the opposed cut-outs are configured such that the injectable material introduced through the driver and into the inner lumen of the suture anchor can flow through the cut-outs.

5. The apparatus of claim 1, wherein the distal end of the elongate shaft includes opposed cut-outs formed therein for allowing a suture extending from the suture anchor to extend externally along the elongate shaft of the driver.

6. The apparatus of claim 1, wherein the distal end of the elongate shaft has a hexagonal cross-sectional shape, and wherein at least a proximal portion of the inner lumen the suture anchor has a complementary hexagonal cross-sectional shape.

7. The apparatus of claim 1, wherein the inner lumen of the suture anchor has a first diameter in the proximal portion thereof, and a second diameter in a distal portion of the inner lumen of the suture anchor, the second diameter being less than the first diameter.

8. The apparatus of claim 7, wherein the second diameter is less than a third diameter of the distal end of the driver such that the distal end of the driver cannot be received within the distal portion of the inner lumen of the suture anchor.

9. The apparatus of claim 1, wherein the inner lumen of the suture anchor has a first cross-sectional shape proximal to the suture-engaging member and a second, different cross-sectional shape distal to the suture-engaging member.

10. The apparatus of claim 1, wherein the driver has a first terminal end of a flexible wire attached thereto, a second terminal end of the flexible wire being coupled to one of the trailing ends of the suture, and the flexible wire being disposed in the inner lumen of the suture anchor and extending around the suture-engaging member.

11. The apparatus of claim 10, wherein, when the flexible wire is disposed in the inner lumen of the suture anchor and extends around the suture-engaging member, the suture does not extend around the suture-engaging member.

12. The apparatus of claim 1, wherein a distal portion of the elongate shaft of the driver has a diameter smaller than a diameter of a proximal portion of the elongate shaft of the driver such that the proximal portion cannot be advanced into the inner lumen of the suture anchor.

13. An apparatus for anchoring tissue to bone, comprising:
a suture anchor having an inner lumen extending between proximal and distal ends thereof, the distal end including opposed cut-outs formed in opposed sidewalls thereof and a suture-engaging member extending between the opposed sidewalls and adjacent to the opposed cut-outs such that a suture can extend around the suture-engaging member and trailing ends of the suture can extend through the inner lumen of the suture anchor, the suture-engaging member being at a non-removably fixed longitudinal position relative to the opposed sidewalls; and
a driver having an elongate shaft and a distal tip, the distal tip being adapted to be received within the proximal end of the suture anchor and advanced distally through the inner lumen to extend through a substantial length of the inner lumen, and the driver having a stop surface formed thereon such that the distal tip is prevented from extending through the inner lumen distally beyond a proximal end of the cut-outs when the driver is being advanced distally into the inner lumen so as to abut the stop surface against the suture anchor.

14. The apparatus of claim 13, wherein the inner lumen of the suture anchor has a first cross-sectional shape proximal to the proximal end of the cut-outs and a second, different cross-sectional shape distal to the proximal end of the cut-outs, the distal tip having a third cross-sectional shape corresponding to the first cross-sectional shape.

15. The apparatus of claim 14, wherein the first and third cross-sectional shapes are hexagonal.

16. The apparatus of claim 13, wherein the elongate shaft includes an inner lumen extending therethrough for receiving a suture extending through the inner lumen of the suture anchor.

17. The apparatus of claim 13, wherein the distal tip includes opposed cut-outs formed therein for allowing a suture extending from the suture anchor to extend externally along the distal tip of the driver.

18. The apparatus of claim 13, wherein the stop surface is configured to abut against an exterior surface of the suture anchor to prevent the distal tip from extending through the inner lumen distally beyond a proximal end of the cut-outs.

\* \* \* \* \*